US00PP19167P2

(12) United States Plant Patent
Cunneen

(10) Patent No.: US PP19,167 P2
(45) Date of Patent: Sep. 2, 2008

(54) ***ARGYRANTHEMUM* PLANT NAMED 'PB1V2'**

(50) Latin Name: *Argyranthemum frutescens*
Varietal Denomination: PB1V2

(75) Inventor: Thomas Cunneen, Balmoral Village (AU)

(73) Assignee: Amerinova Properties LLC, Bonsall, CA (US)

( * ) Notice: Subject to any disclaimer, the term of this patent is extended or adjusted under 35 U.S.C. 154(b) by 0 days.

(21) Appl. No.: 11/800,783

(22) Filed: May 7, 2007

(51) Int. Cl.
*A01H 5/00* (2006.01)

(52) U.S. Cl. ..... Plt./406
(58) Field of Classification Search ..... Plt./406
See application file for complete search history.

*Primary Examiner*—Annette H Para
(74) *Attorney, Agent, or Firm*—C. A. Whealy

(57) ABSTRACT

A new and distinct cultivar of *Argyranthemum* plant named 'PB1V2', characterized by its compact, uniform, outwardly spreading and mounded plant habit; freely branching growth habit; freely flowering habit; anemone-type inflorescences with pale yellow-colored ray florets and golden yellow-colored disc florets; and good garden performance.

1 Drawing Sheet

Botanical designation: *Argyranthemum frutescens.*
Cultivar denomination: 'PB1V2'.

BACKGROUND OF THE INVENTION

The present invention relates to a new and distinct cultivar of *Argyranthemum* plant, botanically known as *Argyranthemum frutescens* and hereinafter referred to by the name 'PB1V2'.

The new *Argyranthemum* is a naturally-occurring whole plant mutation of a proprietary selection of *Argyranthemum frutescens* identified as code number X98060.3, not patented. The new *Argyranthemum* was discovered and selected by the Inventor as a single plant within a population of plants of the selection X98060.3 in a controlled environment Balmoral Village, New South Wales, Australia in October, 2002.

Asexual reproduction of the new *Argyranthemum* by vegetative tip cuttings in a controlled environment in Balmoral Village, New South Wales, Australia since 2002 has shown that the unique features of this new *Argyranthemum* are stable and reproduced true to type in successive generations.

SUMMARY OF THE INVENTION

Plants of the cultivar PB1V2 have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PB1V2'. These characteristics in combination distinguish 'PB1V2' as a new and distinct potted *Argyranthemum* cultivar:

1. Compact, uniform, outwardly spreading and mounded plant habit.
2. Freely branching growth habit.
3. Freely flowering habit.
4. Anemone-type inflorescences with pale yellow-colored ray florets and golden yellow-colored disc florets.
5. Good garden performance.

Plants of the new *Argyranthemum* differ from plants of the parent selection in the following characteristics:

1. Plants of the new *Argyranthemum* are more compact than plants of the parent selection.
2. Plants of the new *Argyranthemum* have anemone-type inflorescences whereas plants of the parent selection have single-type inflorescences.

Plants of the new *Argyranthemum* can be compared to plants of the *Argyranthemum* cultivar Midas Gold, disclosed in U.S. Plant Pat. No. 11,773. In side-by-side comparisons conducted in Balmoral Village, New South Wales, Australia, plants of the new *Argyranthemum* differed from plants of the cultivar Midas Gold in the following characteristics:

1. Plants of the new *Argyranthemum* were shorter than plants of the cultivar Midas Gold.
2. Plants of the new *Argyranthemum* had anemone-type inflorescences whereas plants of the cultivar Midas Gold had single-type inflorescences.

BRIEF DESCRIPTION OF THE PHOTOGRAPHS

The accompanying photographs illustrate the overall appearance of the new *Argyranthemum.* These photographs show the colors as true as it is reasonably possible to obtain in colored reproductions of this type. Colors in the photographs may differ slightly from the color values cited in the detailed botanical description which accurately describe the colors of the new *Argyranthemum.*

The photograph at the bottom of the sheet comprises a side perspective view of a typical flowering plant of 'PB1V2'.

The photograph at the top of the sheet is a close-up view of typical inflorescences of 'PB1V2'.

DETAILED BOTANICAL DESCRIPTION

The aforementioned photographs and following observations and measurements describe plants grown in an outdoor nursery during the summer in Bonsall, Calif. and under conditions and practices which approximate those generally used in commercial potted *Argyranthemum* production. During the production of the plants, day temperatures ranged from about 18° C., to about 38° C., and night temperatures ranged from about 16° C. to 24° C. Plants were pinched one time. Plants used in the photographs and for the description were about nine weeks old. In the following description, color references are made to The Royal Horticultural Society Colour Chart, 1995 Edition, except where general terms of ordinary dictionary significance are used.

Botanical classification: *Argyranthemum frutescens* cultivar PB1V2.

Parentage: Naturally-occurring whole plant mutation of a proprietary selection of *Argyranthemum frutescens* identified as code number X98060.3, not patented.

Propagation:

*Type.*—Terminal cuttings.

*Time to initiate roots, summer.*—About 10 days at temperatures of 25° C.

*Time to initiate roots, winter.*—About 15 days at temperatures of 20° C.

*Time to produce a rooted young plants, summer.*—About 15 days at temperatures of 25° C.

*Time to produce a rooted young plants, winter.*—About 20 days at temperatures of 20° C.

*Root description.*—Fibrous; white in color.

*Rooting habit.*—Moderate branching; moderately dense.

Plant description:

*Appearance.*—Herbaceous anemone-type potted *Argyranthemum.* Compact, uniform, outwardly spreading and mounded plant habit. Strong and freely branching growth habit with eight to nine lateral branches and secondary branches potentially developing at every node; dense and full plants. Vigorous growth habit.

*Plant height.*—About 23 cm.

*Plant width.*—About 34 cm.

*Lateral branches.*—Length: About 23 cm. Diameter: About 4 mm. Internode length: About 7 mm. Strength: Strong. Texture: Smooth, glabrous. Color: 144B.

Foliage description:

*Arrangement.*—Alternate, simple.

*Length.*—About 3.8 cm.

*Width.*—About 2.6 cm.

*Shape.*—Deeply dissected with five lobes.

*Apex.*—Broadly acute.

*Base.*—Attenuate.

*Margin.*—Pinnatifid; entire.

*Texture, upper and lower surfaces.*—Smooth, glabrous.

*Venation pattern.*—Pinnate.

*Color.*—Developing and fully expanded foliage, upper surface: 137A; venation, 137B. Developing and fully expanded foliage, lower surface: 137B; venation, 147B.

*Petiole length.*—About 2.3 cm.

*Petiole diameter.*—About 3 mm.

*Petiole texture, upper and lower surfaces.*—Smooth, glabrous.

*Petiole color, upper and lower surfaces.*—144A.

Inflorescence description:

*Appearance.*—Anemone-type inflorescence form with ligulate-shaped ray florets. Inflorescences borne on terminal and axillary peduncles above foliage. Disk and ray florets arranged acropetally on a capitulum. Inflorescences faintly fragrant; sour.

*Flowering season.*—Plants flower from spring to early fall in Southern California; flowering continuous during this period.

*Inflorescence longevity.*—Inflorescences last about 10 to 14 days on the plant; inflorescences persistent.

*Quantity of inflorescences.*—Freely flowering, about 150 inflorescences develop per plant.

*Inflorescence bud.*—Height: About 1.3 cm. Diameter: About 7 mm. Shape: Elongated ovate. Color: 10C.

*Inflorescence size.*—Diameter: About 3.6 cm. Depth (height): About 1.3 cm. Diameter of disc: About 2.3 cm. Receptacle height: About 6 mm. Receptacle diameter: About 1.4 cm.

*Ray florets.*—Shape: Ligulate to oblong. Orientation: Initially upright, then perpendicular to the peduncle; eventually reflexing with development. Length: About 1.5 cm. Width: About 4 mm. Apex: Emarginate. Base: Acute. Margin: Entire. Texture, upper and lower surfaces: Smooth, glabrous. Number of ray florets per inflorescence: About 20 arranged in a single whorl. Color: When opening, upper surface: 10C. When opening, lower surface: 10D. Fully opened, upper surface: 10D. Fully opened, lower surface: 4D.

*Disc florets.*—Arrangement: Massed at center of receptacle. Shape: Tubular, enlarged. Apex: Five-pointed. Length: About 8 mm. Width, at apex: About 2.5 mm to 3 mm. Width, at base: About 1 mm. Number of disc florets per inflorescence: About 170. Color, immature: Apex: 176A. Mid-section: 177D. Base: 145C. Color, mature: Apex: 12A. Mid-section: 12C. Base: 145B.

*Phyllaries.*—Number of phyllaries per inflorescence: About 24 in three or four whorls. Length: About 4.5 mm. Width: About 2.5 mm. Shape: Elliptic. Apex: Acute. Base: Truncate. Margin: Entire. Texture, upper and lower surfaces: Smooth, glabrous. Color, upper and lower surfaces: 144A.

*Peduncles.*—Length, terminal peduncle: About 6.6 cm. Length, fourth peduncle: About 9 cm. Diameter: About 1.5 mm. Angle: Erect to about 45° from vertical. Strength: Strong, flexible. Texture: Smooth, glabrous. Color: 144A.

*Reproductive organs.*—Androecium: Quantity per disc floret: Five. Filament length: About 1 mm. Filament color: Close to 145D. Anther shape: Lanceolate. Anther length: About 1 mm. Anther color: Close to 177B. Pollen amount: None observed. Gynoecium: Pistil length: About 7 mm. Stigma shape: Two-parted. Stigma color: 13B. Style length: About 3 mm. Style color: 145B. Ovary color: 145C.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about −5° C. to about 40° C.

It is claimed:

1. A new and distinct *Argyranthemum* plant named 'PB1V2' as illustrated and described.

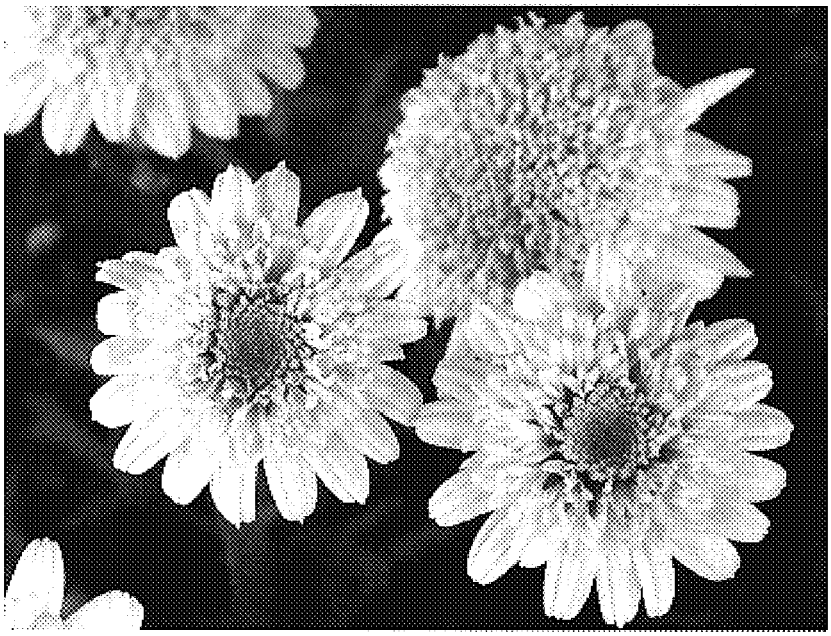
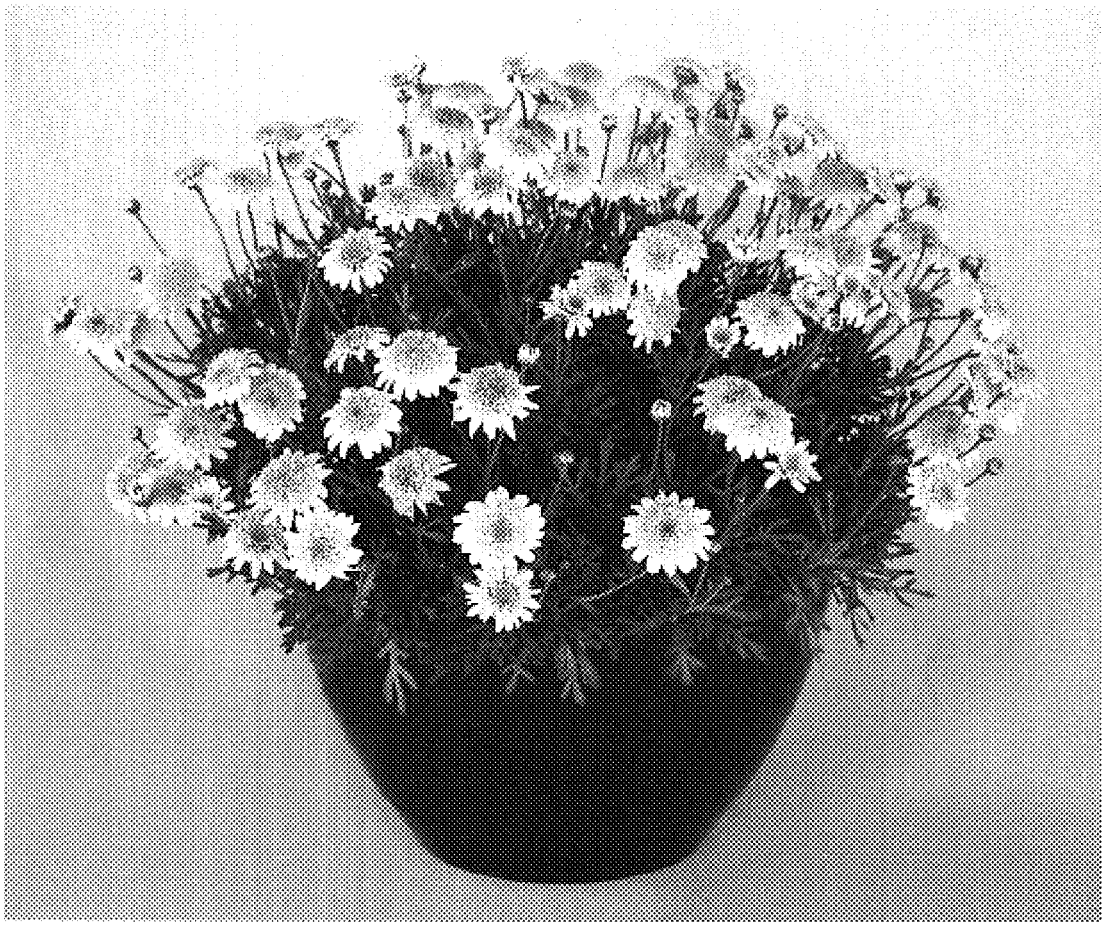

* * * * *